US007381832B2

(12) United States Patent
Lange et al.

(10) Patent No.: US 7,381,832 B2
(45) Date of Patent: Jun. 3, 2008

(54) POLYHALOGEN-SUBSTITUTED CINNAMIC ACIDS AND CINNAMIC ACID DERIVATIVES AND A PROCESS FOR THE PREPARATION OF POLYHALOGEN-SUBSTITUTED CINNAMIC ACIDS AND CINNAMIC ACID DERIVATIVES

(75) Inventors: Walter Lange, Odenthal (DE); Joachim Komoschinski, Köln (DE); Markus Eckert, Köln (DE); Michael Dockner, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 11/150,721

(22) Filed: Jun. 10, 2005

(65) Prior Publication Data

US 2005/0234264 A1 Oct. 20, 2005

Related U.S. Application Data

(62) Division of application No. 10/074,180, filed on Feb. 12, 2002, now Pat. No. 6,956,129.

(30) Foreign Application Priority Data

Feb. 16, 2001 (DE) ............... 101 07 151
Apr. 29, 2001 (DE) ............... 101 15 405
Oct. 25, 2001 (DE) ............... 101 52 789

(51) Int. Cl.
C07C 69/76 (2006.01)
C07C 63/64 (2006.01)
C07C 233/00 (2006.01)

(52) U.S. Cl. .............. 560/104; 562/496; 564/182
(58) Field of Classification Search ........ 560/104; 562/496; 564/182
See application file for complete search history.

(56) References Cited

U.S. PATENT DOCUMENTS

| | | | | |
|---|---|---|---|---|
| 4,979,982 A * | 12/1990 | Brouwer et al. | ............ | 504/243 |
| 5,068,371 A | 11/1991 | Steiner et al. | ............ | 556/53 |
| 5,486,541 A | 1/1996 | Sterling et al. | ............ | 514/657 |
| 5,508,402 A | 4/1996 | Baumeister et al. | ........ | 544/206 |
| 5,637,763 A | 6/1997 | Baumeister et al. | .......... | 562/83 |
| 5,677,306 A | 10/1997 | Aloup et al. | ............ | 514/250 |
| 5,708,033 A | 1/1998 | Kelley et al. | ............ | 514/617 |
| 5,753,655 A | 5/1998 | Combs | ............ | 514/248 |
| 5,869,640 A | 2/1999 | Beach | ............ | 536/23.7 |
| 5,869,657 A | 2/1999 | Annis et al. | ............ | 544/66 |
| 5,872,118 A | 2/1999 | Kelley et al. | ............ | 514/231.2 |
| 5,889,169 A | 3/1999 | Beach et al. | ............ | 536/23.5 |
| 5,998,582 A | 12/1999 | Beach | ............ | 530/350 |
| 6,018,071 A | 1/2000 | Annis et al. | ............ | 560/80 |
| 6,066,501 A | 5/2000 | Beach | ............ | 435/455 |
| 6,080,856 A | 6/2000 | Annis et al. | ............ | 544/66 |
| 6,156,876 A | 12/2000 | Beach | ............ | 530/350 |
| 6,232,489 B1 | 5/2001 | Annis et al. | ............ | 560/28 |
| 6,956,129 B2 * | 10/2005 | Lange et al. | ............ | 560/104 |

FOREIGN PATENT DOCUMENTS

| | | | |
|---|---|---|---|
| GB | 1 445 707 | | 8/1976 |
| JP | 6-263663 | | 9/1994 |
| WO | 00/08023 | | 2/2000 |
| WO | WO 00/07993 | * | 2/2000 |

OTHER PUBLICATIONS

Monatshefte fur Chemie, vol. 90, (month unavailable) 1959, pp. 680-682, Über 2, 4-Difluorzimtsaure by Gunther Lock.
Russian Journal of Organic Chemistry, vol. 33, No. 4, (month unavailable) 1997, pp. 563-564, Synthesis of Fluorine-Substituted Cinnamic Acids by Cross-Coupling of Fluorobenzenes with Acrylic Acid in the Presence of a Palladium Calalyst by A. Ya.Aizikovich and V.Yu.Korotaev.
Waterlot C et al: "Montmorillonite-palladium copper catalyzed cross-coupling of methyl acrylate with aryl amines", Tetrahedron Letters, Elsevier Science Publishers, Amsterdam, NL, Bd. 41, Nr. 3, Jan. 2000, Seiten 317-319, XP004186256, ISSN: 0040-4039 das ganze dokument.
Kikukawa K et al: "Palladium(0)-Catalyzed Arylation Of Olefins By Arylmines and an Alkyl Nitrate" Journal of Organic Chemistry, American Chemical Society. Easton, US, Bd. 46, 1981, Seiten 4885-4888, XP000882385 ISSN: 0022-3263 Tabelle III.
Database Crossfire Beilstein 'Online! Bellstein Institut zur Förderung der Chemischen Wissenschaften, Frankfurt am Main, DE; Database accession No. 3474443 XP002207216 , Zusammenfassung & Kruse, L I et al: Journal of Medicinal Chemistry., Bd. 30, Nr. 3, 1987, Seiten 486-494, American Chemical Society., US ISSN: 0022-2623.
Database Crossfire Beilstein 'Online! Beilstein Institut zur Förderung der Chemischen Wissenschaften, Frankfurt am Main, DE; Database accession No. 1041035 XP002207217 Zusammenfassung & Berrier, C Et Al: Tetrahedron Bd. 40, Nr. 23, 1984, Seiten 4973-4980, Elsevier Science Publishers, Amsterdam., NL ISSN: 0040-4020.
Database Crossfire Beilstein 'Online! Beilstein Institut zur Förderung der Chemischen Wissenschaften, Frankfurt am Main, DE; Database accession No. 1053433 XP002207218 Zusammenfassung Simchen, G et al: Journal of Medicinal Chemistry., Bd. 15, 1972, Seiten 341-344, American Chemistry Society., US ISSN: 0022-2623.

(Continued)

Primary Examiner—Taylor Victor Oh
(74) Attorney, Agent, or Firm—Michael A. Miller

(57) ABSTRACT

Polyhalogenated cinnamic acids and cinnamic acid derivatives are prepared by reacting diazonium salts accessible from polyhalogenated anilines with acrylic acid or acrylic acid derivatives in the presence of a homogeneous, palladium-containing catalyst at about −5 to about +100° C. Some of the cinnamic acids and cinnamic acid derivatives obtainable in this way are new. Cinnamic acids and cinnamic acid derivatives which can be prepared according to the invention can be used for the preparation of indanones which are precursors for agro- and pharmaceutical chemicals and for substances having liquid-crystalline properties.

7 Claims, No Drawings

OTHER PUBLICATIONS

Database Crossfire Beilstein 'Online! Beilstein Institut zur Förderung der Chemischen Wissenschaften, Frankfurt am Main, DE; Database accession No. 665237 XP002207219 Zusammenfassung & Hussey, H: Journal of Organic Chemistry., Bd. 24, 1959, Seite 843 American Chemical Society, Washington, D.C., US ISSN: 0022-3263.

Sengupta S Et Al: "Heck reaction of arenediazonium salts: a palladium-catalysed reaction in an aqueous medium" Journal of the Chemical Society, Perkin Transactions 1, Chemical Society. Letchworth, GB, Nr. 17 Sep. 7, 1993, Seiten 1943-1944, XP002128192 ISSN: 1472-7781 Scheme 1, Verbindungen 1b-3b Scheme 2.

* cited by examiner

POLYHALOGEN-SUBSTITUTED CINNAMIC ACIDS AND CINNAMIC ACID DERIVATIVES AND A PROCESS FOR THE PREPARATION OF POLYHALOGEN-SUBSTITUTED CINNAMIC ACIDS AND CINNAMIC ACID DERIVATIVES

This application is a Divisional of Ser. No. 10/074,180 filed Feb. 12, 2002 now U.S. Pat. No. 6,956,129.

BACKGROUND

The present invention relates to new polyhalogen-substituted cinnamic acids and cinnamic acid derivatives and a process for the preparation of known and new polyhalogen-substituted cinnamic acids and cinnamic acid derivatives.

Known halogen-substituted cinnamic acids and cinnamic acid derivatives are intermediates for the production of agrochemicals and pharmaceuticals (see DE-A 22 44 761, WO 95/30645, WO 94/26692, WO 94/7893, WO 94/26693 and U.S. Pat. No. 5,753,655).

2,4-Difluorocinnamic acid and its esters of the formula (II) can be prepared by reacting benzyl halides of the formula (I) with acetic anhydride or benzaldehydes of the formula (I) with malonic acid or malonic acid esters.

The following reaction equation illustrates this:

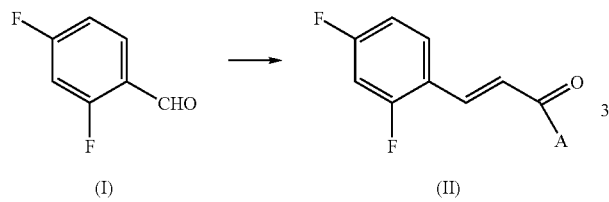

A=OH or O-alkyl.

A disadvantage here is the high reaction temperature needed, the unsatisfactory yield and the difficult accessibility of the compounds of the formula (I). Monatshefte der Chemie 90, 680 (1959) describes the reaction of 2,4-difluorobenzaldehyde with acetic anhydride at 180° C., 2,4-difluoro-cinnamic acid being obtained in a 77% yield.

In another route for the preparation of a halogen-substituted cinnamic acid derivative, 2,4-difluoro-bromobenzene is used as a starting material and this is reacted with acrylic acid with addition of triphenylphosphinepalladium dichloride and potassium carbonate in dimethylformamide at 145 to 150° C. in the course of 6 hours. The corresponding cinnamic acid derivative is obtained in a yield of only 54% (Russ. J. Org. Chem. 33 (4), 563-569 (1997)). The yield is still unsatisfactory here and high reaction temperatures and long reaction times are also needed.

Finally, it is known from EP-A-584 043 that compounds of the type Ar—CHR$_a$—CHR$_b$R$_c$ can be prepared if diazonium salts of the type AR—N$_2$⊕ are reacted with compounds of the type CR$_a$=CR$_b$R$_c$ with formation of compounds of the type Ar—CHR$_a$=CR$_b$R$_c$ and the reaction is carried out in the presence of homogeneous palladium catalysts and with addition of 1 to 10 equivalents of base. This process is particularly suitable for the preparation of compounds in which the Ar radical is substituted by a sulfonic acid group, i.e. a strongly polar group. In addition to this restriction, it is disadvantageous that in this process large amounts of bases have to be added, which means additional costs and makes necessary a complicated work-up of the reaction mixture.

EP-A-584 264 describes a similar process to that of EP-A-584 043. However, the reaction is carried out in the additional presence of arylphosphanes, which is associated with further costs and further additional outlay.

There is thus still the need for a process for the preparation of polyhalogenated cinnamic acids and cinnamic acid derivatives in which, in a simple manner, at moderate temperatures, with short reaction times, without addition of base and without necessary addition of arylphosphanes, the desired products are accessible in a higher yield than hitherto.

SUMMARY

The invention relates to a process for preparing a polyhalogenated cinnamic acid or a cinnamic acid derivative having the formula (III)

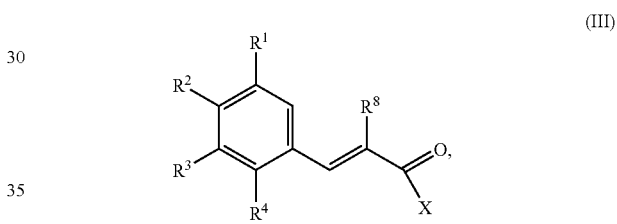

wherein $R^1$, $R^2$, $R^3$ and $R^4$ are identical or different and in each case represent hydrogen, fluorine, chlorine or bromine, at least two of these radicals being other than hydrogen and X represents $OR^5$ or $N(R^6)(R^7)$ where $R^5$ represents hydrogen or optionally substituted $C_1$-$C_{10}$-alkyl, optionally substituted phenyl or benzyl and $R^6$ and $R^7$ are identical or different and in each case represent optionally substituted $C_1$-$C_{10}$-alkyl and $R^8$ represents hydrogen, chlorine, bromine or optionally substituted $C_1$-$C_{10}$-alkyl. The process comprises reacting (1) a diazonium salt of the formula (IV)

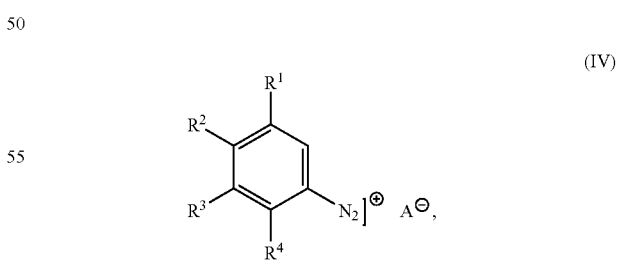

wherein $R^1$, $R^2$, $R^3$ and $R^4$ have the meaning indicated in formula (III) and $A^\ominus$ represents an equivalent of halide, hydrogensulfate, nitrate, acetate or tetrafluoroborate ions or ½ an equivalent of sulfate ions or ⅓ an equivalent of phosphate ions, with (2) an acrylic acid or an acrylic acid derivative of the formula (V)

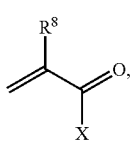

(V)

wherein X has the meaning indicated in formula (III) and $R^8$ represents hydrogen, chlorine, bromine or optionally substituted $C_1$-$C_{10}$-alkyl, in the presence of a homogeneous, palladium-containing catalyst at a temperature ranging from about −5 to about +100° C. The invention also relates to a polyhalogenated cinnamic acid or a cinnamic acid derivative having the formula (III'):

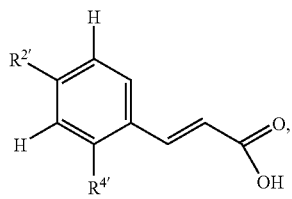

(III')

wherein $R^{2'}$ represents chlorine and $R^{4'}$ represents fluorine, or $R^{2'}$ represents fluorine and $R^{4'}$ represents chlorine.

The invention also relates to a method for preparing an indanone derivative of the formula (VIIa):

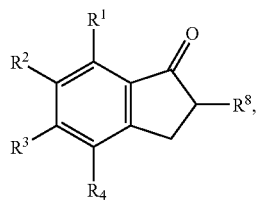

(VIIa)

wherein $R^1$, $R^2$, $R^3$ and $R^4$ are identical or different and in each case represent hydrogen, fluorine, chlorine or bromine, at least two of these radicals being other than hydrogen and $R^8$ represents hydrogen, chlorine, bromine or optionally

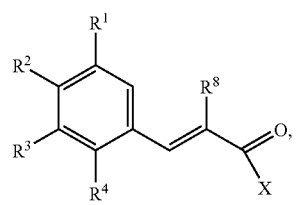

(III)

wherein $R^1$, $R^2$, $R^3$, $R^4$ are identical or different and in each case represent hydrogen, fluorine, chlorine or bromine, at least two of these radicals being other than hydrogen and X represents $OR^5$ or $N(R^6)(R^7)$, where $R^5$ represents hydrogen or optionally substituted $C_1$-$C_{10}$-alkyl, optionally substituted phenyl or benzyl and $R^6$ and $R^7$ are identical or different and in each case represent optionally substituted $C_1$-$C_{10}$-alkyl and $R^8$ represents hydrogen, chlorine, bromine or optionally substituted $C_1$-$C_{10}$-alkyl, and (b) cyclizing the hydrogenated cinnamic acid or cinnamic acid derivative formed in step (a), thereby forming the indanone derivative of the formula (VIIa).

The invention also relates to a method for method for preparing an indanone derivative of the formula (VIIb)

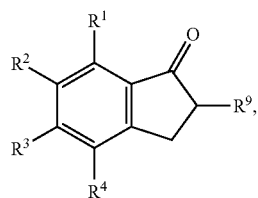

(VIIb)

wherein $R^1$, $R^2$, $R^3$ and $R^4$ are identical or different and in each case represent hydrogen, fluorine, chlorine or bromine, at least two of these radicals being other than hydrogen and $R^9$ represents COOH, $CONH_2$ or $COOR^{10}$, wherein $R^1$ denotes $C_1$-$C_4$-alkyl. The method comprises (a) hydrogenating a polyhalogenated cinnamic acid or cinnamic acid derivative having the formula (III)

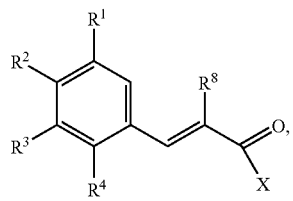

(III)

wherein $R^1$, $R^2$, $R^3$, $R^4$ are identical or different and in each case represent hydrogen, fluorine, chlorine or bromine, at least two of these radicals being other than hydrogen and X represents $OR^5$ or $N(R^6)(R^7)$, where $R^5$ represents hydrogen or optionally substituted $C_1$-$C_{10}$-alkyl, optionally substituted phenyl or benzyl and $R^6$ and $R^7$ are identical or different and in each case represent optionally substituted $C_1$-$C_{10}$-alkyl and $R^8$ represents hydrogen, chlorine or bromine, and (b) cyclizing the hydrogenated cinnamic acid or cinnamic acid derivative formed in step (a), thereby forming the indanone derivative of the formula (VIIa)

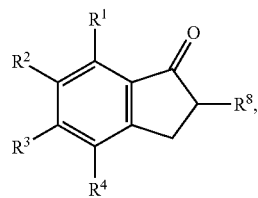

(VIIa)

wherein $R^1$, $R^2$, $R^3$, $R^4$ and $R^8$ have the meaning indicated in formula (III) above and (c) converting the indanone derivative of the formula (VIIa), in case of $R^8$ representing hydrogen after halogenation, by a palladium-catalysed carbonylation reaction with carbon monoxide and a suitable nucleophile, and thereby forming the indanone derivative of the formula (VIIb).

These and other features, aspects, and advantages of the present invention will become better understood with reference to the following description and appended claims.

DESCRIPTION

A process for the preparation of polyhalogenated cinnamic acids and cinnamic acid derivatives of the formula (III) has now been found

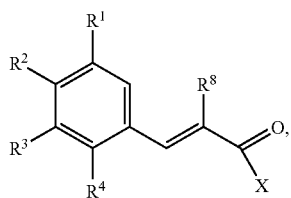

(III)

in which $R^1$, $R^2$, $R^3$ and $R^4$ are identical or different and in each case represent hydrogen, fluorine, chlorine or bromine, at least two of these radicals being other than hydrogen and X represents $OR^5$ or $N(R^6)(R^7)$, where $R^5$ represents hydrogen, optionally substituted $C_1$-$C_{10}$-alkyl, optionally substituted phenyl or benzyl and $R^6$ and $R^7$ are identical or different and in each case represent optionally substituted $C_1$-$C_{10}$-alkyl and $R^8$ represents hydrogen, chlorine, bromine or optionally substituted $C_1$-$C_{10}$-alkyl, which is characterized in that a diazonium salt of the formula (IV)

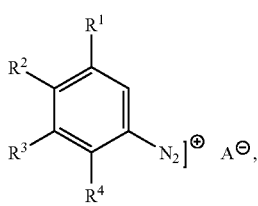

(IV)

in which $R^1$, $R^2$, $R^3$ and $R^4$ have the meaning indicated in formula (III) and $A^\ominus$ represents an equivalent of halide, hydrogensulfate, nitrate, acetate or tetrafluoroborate ions or ½ an equivalent of sulfate ions or ⅓ an equivalent of phosphate ions, is reacted with acrylic acid or an acrylic acid derivative of the formula (V)

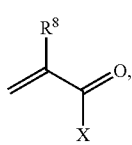

(V)

in which

X has the meaning indicated in formula (III) and $R^8$ represents hydrogen, chlorine, bromine or optionally substituted $C_1$-$C_{10}$-alkyl, in the presence of a homogeneous, palladium-containing catalyst at a temperature ranging from about −5 to about +100° C.

The process according to the invention is most preferably carried out without addition of base. Generally, the process is carried out with 0.5 moles or below, preferably 0.1 moles or below and more preferably 0.05 moles base per mole of diazonium salt of the formula (IV).

Advantageously and most preferably the process according to the invention is carried without the addition of arylphosphanes. Generally, the process is carried out with 4 moles or below, preferably 1 moles or below and more preferably 0.1 moles of arylphosphanes per mole of palladium.

If the radicals $R^5$, $R^6$, $R^7$ and $R^8$ are optionally substituted alkyl radicals, suitable substituents can be, for example, halogen, hydroxyl or $C_6$-$C_{12}$-aryl radicals. 1 or 2 of these substituents can be present, for example, per radical selected from the group consisting of $R^5$, $R^6$, $R^7$ and $R^8$.

Preferably, $R^1$ represents hydrogen or chlorine, $R^2$ represents hydrogen, fluorine, chlorine or bromine, $R^3$ represents hydrogen or chlorine and $R^4$ represents fluorine or chlorine, at least one of the radicals $R^1$, $R^2$ and $R^3$ being other than hydrogen.

$R^5$ preferably represents hydrogen, methyl, ethyl, isopropyl or benzyl. $R^6$ and $R^7$ preferably represent methyl or ethyl. $R^8$ preferably represents hydrogen or methyl. $A^\ominus$ preferably represents an equivalent of chloride, hydrogensulfate or acetate or ½ an equivalent of sulfate.

Suitable homogeneous, palladium-containing catalysts are, for example, palladium(II) and palladium(0) compounds such as $PdCl_2$, $PdBr_2$, $Pd(NO_3)_2$, $H_2PdCl_4$, $Pd(CH_3COO)_2$, $Na_2PdCl_4$, $K_2PdCl_4$, Pd(II) acetylacetonate tetra-(triphenylphosphine)Pd and tris-(dibenzylideneacetone)$Pd_2$. $PdCl_2$, $Pd(CH_3COO)_2$ and Pd(II) acetylacetonate are preferred.

The respective palladium-containing catalyst can be employed, for example, in an amount ranging from about 0.001 to about 10 mol %, preferably based on the diazonium salt of the formula (IV).

Preferred reaction temperatures are those ranging from about +20 to about +80° C., in particular those ranging from about +40 to about +65° C.

The process according to the invention can optionally be carried out with the addition of simple solvents. Suitable simple solvents are, for example, water, alcohols, like for example $C_1$-$C_6$-alkyl alcohols, carboxylic acids, like for example formic acid, ethers, like for example tetrahydrofuran and nitriles, like for example acetonitrile.

The diazonium salts of the formula (IV) can be prepared in a manner known per se (see, for example, Houben-Weyl, Volume X/3, pages 7 to 113) from the corresponding anilines by reaction with sodium nitrite in acidic aqueous solution or by reaction of methyl nitrite in acidic methanol. The diazonium salts can be employed in the process according to the invention in the form of the reaction mixture obtained during their preparation, preferably after the destruction of nitrite which may still be present. Isolation of the diazonium salts is not necessary.

Preferred compounds of the formula (V) are acrylic acid, methacrylic acid, acrylamide and methacrylamide.

Based on 1 mol of diazonium salt of the formula (IV), it is possible to employ, for example, from about 0.5 to about 2 mol of acrylic acid or acrylic acid derivatives of the formula (V). This amount is preferably from about 0.9 to about 1.5 mol.

The process according to the invention can be carried out so that, for example, firstly an aniline of the formula

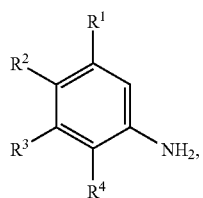

(VI)

in which

R$^1$, R$^2$, R$^3$ and R$^4$ have the meaning indicated in formula (III), is converted with sodium nitrite in aqueous sulfuric acid solution or with an alkyl nitrite such as methyl, ethyl, butyl or amyl nitrite, preferably methyl nitrite, in acidic, e.g. sulfuric acid-containing methanol, into a diazonium salt of the formula (IV), nitrite which may be present in the reaction mixture obtained is destroyed by addition of amidosulfonic acid, the reaction mixture treated in this way is added dropwise at reaction temperature to a mixture of acrylic acid or an acrylic acid derivative of the formula (V) with a homogeneous, palladium-containing catalyst and optionally a simple solvent such as water, methanol, ethanol or isopropanol and optionally after a stirring time the prepared product of the formula (III), if appropriate after cooling and/or dilution with water, is separated off, e.g. by filtration, distillation or phase separation.

The process according to the invention has the advantages that it produces polyhalogen-substituted cinnamic acids and cinnamic acid derivatives in high yields in a simple manner, at low temperatures, in short reaction times, with low amounts or preferably without additions of bases and with low amounts or preferably without additions of arylphosphanes. Moreover, no special solvents such as amidic solvents and especially dimethylformamide are needed.

The present invention further relates to new polyhalogenated cinnamic acids and cinnamic acid derivatives of the formula (III')

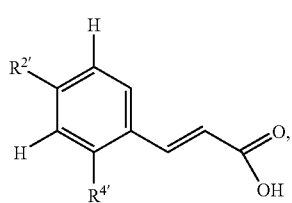

(III')

in which

R$^{2'}$ represents chlorine and R$^{4'}$ represents fluorine or

R$^{2'}$ represents fluorine and R$^{4'}$ represents chlorine.

One possibility of preparation of the new compounds of the formula (III') has been described above. Their utility is illustrated below. The polyhalogenated cinnamic acids and cinnamic acid derivatives of the formula (III) including those of the formula (III') can be converted by hydrogenation of the double bond (1st step) and subsequent cyclization (2nd step) into indanone derivatives of the formula

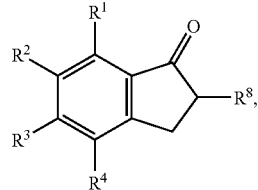

(VIIa)

in which

R$^1$ to R$^4$ have the meaning indicated in formula (III) and

R$_8$ represents hydrogen, bromine, chlorine or optionally substituted C$_1$-C$_{10}$-alkyl. Compounds of the general formula (VIIa) in which R$^8$ represents hydrogen can be converted in a manner known per se by halogenation into the corresponding compounds of the general formula (VIIa) in which R$^8$ represents bromine or chlorine.

Furthermore, compounds of the general formula (VIIa) in which R$^8$ represents bromine or chlorine can be converted in a manner known per se, for example by palladium-catalysed carbonylation reactions with carbon monoxide and a suitable nucleophile, into indanone derivatives of the formula (VIIb)

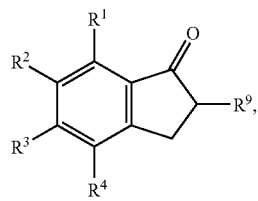

(VIIb)

in which

R$^1$ to R$^4$ have the meaning indicated in formula (III) and

R$^9$ represents COOH, CONH$_2$ or COOR$^{10}$, where

R$^{10}$ denotes C$_1$-C$_4$-alkyl.

The 1st step can be carried out, for example, by hydrogenating with hydrogen in the presence of platinum or palladium, if appropriate at elevated pressure, and the 2nd step can be carried out, for example, by converting the arylproprionic acids obtained into the corresponding acid chlorides and cyclizing these with the aid of Friedel-Crafts catalysts to give the indanones of the general formula (VIIa).

From these indanones and those of the formula (VIIb), agrochemical and pharmaceutical active compounds and liquid-crystalline materials are accessible analogously to known processes (see, for example, WO 95/29171, EP-A 538 134, EP-A 401 166 and JP-A 06-263 663). The new compounds of the formula (III') widen the range of the indanones available and thus to prepare and to test potential active compounds in the agrochemical and pharmaceutical field and also in the field of liquid-crystalline substances.

The invention is further described in the following illustrative examples in which all parts and percentages are by weight unless otherwise indicated.

EXAMPLES

Example 1

2,4-Difluorocinnamic Acid 62 ml of concentrated sulfuric acid were added to 236 ml of water, the mixture was cooled to 5° C. and 38.7 g of 2,4-difluoroaniline were added. A solution of 23.9 g of sodium nitrite in 45 ml of water was added dropwise at 0 to 2° C. in the course of 40 minutes and the mixture was stirred for 30 minutes. Sufficient amidosulfonic acid was then added to destroy excess nitrite. 0.34 g of tris(dibenzylideneacetone)-dipalladium(0) was added to 25.8 g of acrylic acid and the diazonium salt solution was added dropwise at 40° C. over the course of 4 hours and the mixture was stirred for 2 hours. After it had been cooled to room temperature, 47.5 g of difluorocinnamic acid were isolated by filtration (86% of theory; melting point: 203° C.).

Example 2

2,4-Difluorocinnamic Acid 77.5 g of difluoroaniline were added dropwise at 0° C. to a mixture of 124 ml of concentrated sulfuric acid and 472 ml of water. A solution of 48.3 g of sodium nitrite in 90 ml of water was then added dropwise at 0° C. in the course of 30 minutes such that the temperature was maintained. The mixture was then stirred at 0° C. for 30 minutes. Excess nitrite was destroyed by the addition of amidosulfonic acid.

0.1 g of palladium(II) acetylacetonate was added to 54.8 g of acrylic acid and the mixture was warmed to 50° C. The diazonium salt solution was added dropwise at this temperature in the course of 4 hours and the mixture was stirred for a further 2 hours. After it had been cooled to room temperature, the solid was isolated by filtration, washed with water and dried (99.6 g; 90% of theory; melting point: 203 to 205° C.).

Example 3

4-Bromo-2-fluorocinnamic acid 62 ml of sulfuric acid were added to 236 ml of water and the mixture was cooled to 5° C. 57.0 g of 4-bromo-2-fluoroaniline were added at this temperature and a solution of 24.2 g of sodium nitrite in 45 ml of water was added dropwise at 0 to 2° C. in the course of 30 minutes and the mixture was stirred for 20 minutes. 2.8 g of amidosulfonic acid were then added. 5 ml of the diazonium salt solution were added dropwise at 40° C. to 27.5 g of acrylic acid, 0.23 g of palladium(II) acetylacetonate was added and the residual diazonium salt solution was added dropwise in the course of 20 minutes. The mixture was stirred at 40° C. for 4 hours. It was allowed to cool to room temperature and the product was isolated by filtration. After drying, 54.4 g of 4-bromo-2-fluorocinnamic acid were present (74% of theory; melting point: 218° C.).

Example 4

2,4-Dichlorocinnamic Acid

Gaseous methyl nitrite was prepared from 35 g of sodium nitrite in a methanol (20 ml)/water (60 ml) mixture by addition of 30 ml of 50% strength sulfuric acid (30 ml), and was introduced at 0° C. into a mixture of 250 ml of water, 60 ml of conc. sulfuric acid and 53.5 g of 2,4-dichloroaniline. The mixture was stirred for 1 hour. Excess methyl nitrite was removed by passing through a stream of nitrogen and addition of 3 g of amidosulfonic acid. This solution was added over the course of 2 hours at 40° C. to a solution of 0.25 g of palladium(II) acetylacetonate and 30 g of acrylic acid and the mixture was stirred for 2 hours. After cooling to room temperature, the precipitate was filtered and dried. 58.1 g of 2,4-dichlorocinnamic acid resulted (81% of theory; melting point: 230° C.).

Example 5

2,4-Difluorocinnamic Acid 77.5 g of difluoroaniline were added dropwise at 0° C. to a mixture of 124 ml of conc. sulfuric acid and 472 ml of water. A solution of 48.3 g of sodium nitrite in 90 ml of water was then added dropwise at 0° C. such that the temperature was maintained. The mixture was then stirred at 0° C. for 30 minutes. Excess nitrite was destroyed by the addition of amidosulfonic acid.

0.34 g of palladium(II) acetate was added to 54.8 g of acrylic acid and the mixture was warmed to 47° C. The diazonium salt solution was added dropwise at this temperature in the course of 2 hours such that the temperature did not exceed 49° C., then the mixture was stirred for a further 2 hours. After it had been cooled to room temperature, the solid was isolated by filtration, washed with water and dried. This afforded 105.1 g of 2,4-difluorocinnamic acid (95% of theory; melting point 204-205° C.).

Example 6

3-(2,4-Difluorophenyl)-2-methylacrylic Acid 77.5 g of difluoroaniline were added dropwise at 0° C. to a mixture of 124 ml of conc. sulfuric acid and 472 ml of water. A solution of 48.3 g of sodium nitrite in 90 ml of water was then added dropwise at 0° C. such that the temperature was maintained, then the mixture was stirred at 0° C. for 30 minutes. Excess nitrite was destroyed by the addition of amidosulfonic acid.

0.34 g of palladium(II) acetate was added to 60.1 g of methacrylic acid and the mixture was warmed to 45° C. The diazonium salt solution was added dropwise at this temperature in the course of 2 hours such that the temperature did not exceed 50° C., then the mixture was stirred for a further 2 hours. After it had been cooled to room temperature, the solid was isolated by filtration, washed with water and dried. 118.0 g of 3-(2,4-difluorophenyl)-2-methylacrylic acid resulted (85% of theory; melting point 140-142° C.).

Example 7

3-(2,4-Difluorophenyl)-propionic Acid (Not According to the Invention)

105 g of 2,4-difluorocinnamic acid from Example 5 were dissolved in 450 ml of tetrahydrofuran and reacted with 5 g of palladium on active carbon with stirring at 100° C. and a hydrogen pressure of 50 bar. After a constant pressure had been achieved, the mixture was cooled to room temperature, the pressure was released, the palladium catalyst was filtered off and the solvent was removed by distillation. After drying in vacuo, 104.1 g of 3-(2,4-difluorophenyl)-propionic acid (98% of theory; melting point: 100-102° C.) were obtained.

Example 8

2,5-Difluoro-4-chlorocinnamic Acid 98.2 g of 2,5-difluoro-4-chloroaniline were added dropwise at 0° C. to a mixture of 124 ml of conc. sulfuric acid and 472 ml of water. A solution of 48.3 g of sodium nitrite in 90 ml of water was then added dropwise at 0° C. such that the temperature was maintained. The mixture was then stirred at 0° C. for 30 minutes. Excess nitrite was destroyed by the addition of amido-sulfonic acid.

0.34 g of palladium(II) acetate was added to 54.8 g of acrylic acid and the mixture was warmed to 47° C. The diazonium salt solution was added dropwise at this temperature in the course of 2 hours such that the temperature did not exceed 49° C., then the mixture was stirred for a further 2 hours. After it had been cooled to room temperature, the solid was isolated by filtration, washed with water and dried. This afforded 116.7 g of 2,5-difluoro4-chlorocinnamic acid (89% of theory).

Example 9

2,5-Difluoro-3-chlorocinnamic acid 98.2 g of 2,5-difluoro-3-chloroaniline were added dropwise at 0° C. to a mixture of 124 ml of conc. sulfuric acid and 472 ml of water. A solution of 48.3 g of sodium nitrite in 90 ml of water was then added dropwise at 0° C. such that the temperature was maintained. The mixture was then stirred at 0° C. for 30 minutes. Excess nitrite was destroyed by the addition of amidosulfonic acid.

0.34 g of palladium(II) acetate was added to 54.8 g of acrylic acid and the mixture was warmed to 47° C. The diazonium salt solution was added dropwise at this temperature in the course of 2 hours such that the temperature did not exceed 49° C., then the mixture was stirred for a further 2 hours. After it had been cooled to room temperature, the solid was isolated by filtration, washed with water and dried. This afforded 108.9 g of 2,5-difluoro-3-chlorocinnamic acid (83% of theory).

Example 10

2,3,4,5-Tetrachlorocinnamic Acid 98.2 g of 2,3,4,5-tetrachloroaniline were added dropwise at 0° C. to a mixture of 124 ml of conc. sulfuric acid and 472 ml of water. A solution of 48.3 g of sodium nitrite in 90 ml of water was then added dropwise at 0° C. such that the temperature was maintained. The mixture was then stirred at 0° C. for 30 minutes. Excess nitrite was destroyed by the addition of amidosulfonic acid.

0.34 g of palladium(II) acetate was added to 54.8 g of acrylic acid and the mixture was warmed to 47° C. The diazonium salt solution was added dropwise at this temperature in the course of 2 hours such that the temperature did not exceed 49° C., then the mixture was stirred for a further 2 hours. After it had been cooled to room temperature, the solid was isolated by filtration, washed with water and dried. This afforded 144.1 g of 2,3,4,5-tetrachlorocinnamic acid (84% of theory).

Example 11

3-(2,4-Difluorophenyl)propionic Acid (Not According to the Invention)

The procedure was as in Example 5, but the 2,4-difluorocinnamic acid obtained was not isolated. The aqueous-acidic product suspension obtained was treated with 2 g of Pd/C (5% strength) at 50° C. with further stirring and heated to 100° C. It was then pressurized to 5 bar of hydrogen. After constant pressure had been achieved, it was cooled to room temperature, the pressure was released and the solid was filtered off. The filter cake was taken up in methylene chloride, the palladium catalyst was filtered off and the solvent was removed. After drying in vacuo, 100.5 g of 3-(2,4-difluorophenyl)propionic acid (90% of theory; melting point: 100° C.) were obtained.

Example 12

3-(2,4-Difluorophenyl)propionic acid (Not According to the Invention)

The procedure was as in Example 11, but the addition of palladium on active carbon was dispensed with. 98.3 g of 3-(2,4-difluorophenyl) propionic acid (88% of theory) were obtained.

Example 13

3-(2,4-Difluorophenyl)propionic Acid (Not According to the Invention)

The procedure was as in Example 5, but the 2,4-difluorocinnamic acid obtained was not isolated. The aqueous-acidic product suspension obtained was rendered alkaline using sodium hydroxide solution and treated with 2 g of Pd/C (5% strength) at 50° C. with further stirring and heated to 100° C. It was then pressurized to 5 bar of hydrogen. After constant pressure had been achieved, it was cooled to room temperature, the pressure was released and the palladium catalyst was filtered off. The alkaline product solution was acidified with sulfuric acid and the product precipitate was isolated by filtration. After drying in vacuo, 95.0 g of 3-(2,4-difluorophenyl)propionic acid (85% of theory) were obtained.

Example 14

4,6-Difluoroindan-1-one (Not According to the Invention)

Thionyl chloride (54.6 g) was added dropwise at 40° C. to a solution of 3-(2,4-di-fluorophenyl)propionic acid (57 g) in methylene chloride (200 ml). After reaction was complete, excess thionyl chloride and the solvent were removed by distillation. The oily residue was added dropwise at 40° C. to a suspension of aluminium chloride (88.5 g) in methylene chloride (200 ml). The reaction mixture was added to dilute hydrochloric acid after 18 hours at 40° C. The aqueous phase was separated off and extracted once with methylene chloride (250 ml). The combined organic phases were freed from the solvent and then distilled in vacuo. 41 g of a colorless solid were obtained (m.p.: 103° C.).

Example 15

4,6-Dichloroindan-1-one (Not According to the Invention)

Thionyl chloride (36.9 g) was added dropwise at 40° C. to a solution of 3-(2,4-di-chlorophenyl)propionic acid (43.8 g) in methylene chloride (200 ml).

After reaction was complete, excess thionyl chloride and the solvent were removed by distillation. The oily residue was added dropwise at 40° C. to a suspension of aluminium chloride (53.3 g) in methylene chloride (200 ml). The reaction mixture was added to dilute hydrochloric acid after 18 hours at 40° C. The aqueous phase was separated off and extracted once with methylene chloride (250 ml). The combined organic phases were freed from the solvent. The residue was recrystallized from cyclohexane. 30 g of a colorless solid (m.p.: 115-116° C.) were obtained.

Example 16

5,7-Dichloroindan-1-one (Not According to the Invention)

Thionyl chloride (45.2 g) was added dropwise at 40° C. to a solution of 3-(3,5-di-chlorophenyl)propionic acid (54.8 g) in methylene chloride (200 ml). After reaction was complete, excess thionyl chloride and the solvent were removed by distillation. The oily residue was added dropwise at 40° C. to a suspension of aluminium chloride (66.7 g) in methylene chloride (200 ml). The reaction mixture was added to dilute hydrochloric acid after 18 hours at 40° C. The aqueous phase was separated off and extracted once with methylene chloride (250 ml). The combined organic phases were freed from the solvent. The residue was recrystallized from cyclohexane. 36 g of a colorless solid (m.p.: 119-120° C.) were obtained.

Example 17

Analogously to Example 5, starting from 2-chloro-5-fluoroaniline, 2-chloro-5-fluorocinnamic acid was prepared in a yield of 80% of theory. The melting point of this cinnamic acid was 182° C. and the $^1$H-NMR spectrum showed characteristic absorptions at 6.6 ppm (d), 7.25 ppm (m), 7.5 ppm (m) and 7.75 (m), recorded in DMSO.

Example 18

Analogously to Example 5, starting from 2-fluoro-5-chloro-aniline, 2-fluoro-5-chloro-cinnamic acid was prepared in a yield of 81% of theory. The melting point of this cinnamic acid was 183° C. and the $^1$H-NMR spectrum showed characteristic absorptions at 6.6 ppm (d), 7.25 ppm (t), 7.45 ppm (m), 7.55 ppm (d) and 7.9 ppm (m), recorded in DMSO.

Although the present invention has been described in detail with reference to certain preferred versions thereof, other variations are possible. Therefore, the spirit and scope of the appended claims should not be limited to the description of the versions contained therein.

What is claimed is:

1. A process for preparing a compound of formula (III)

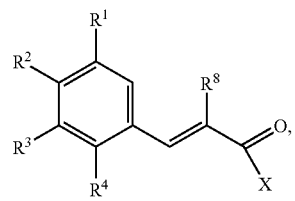

(III)

wherein $R^1$, $R^2$, $R^3$ and $R^4$ are identical or different and in each case represent hydrogen, fluorine, chlorine or bromine, at least two of these radicals being other than hydrogen and X represents $OR^5$ or $N(R^8)(R^7)$, where $R^5$ represents hydrogen or $C_1$-$C_{10}$-alkyl, phenyl or benzyl and $R^6$ and $R^7$ are identical or different and in each case represent $C_1$-$C_{10}$-alkyl and $R^8$ represents hydrogen, chlorine, bromine or optionally substituted $C_1$-$C_{10}$-alkyl, the process comprising: reacting (1) a diazonium salt of the formula (IV)

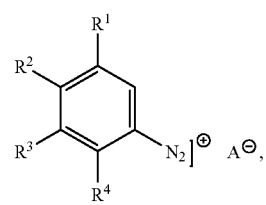

(IV)

wherein $R^1$, $R^2$, $R^3$ and $R^4$ have the meaning indicated in formula (III) and $A^\ominus$ represents an equivalent of halide, hydrogensulfate, nitrate, acetate or tetrafluoroborate ions or ½ an equivalent of sulfate ions or ⅓ an equivalent of phosphate ions, with (2) a compound of the formula (V)

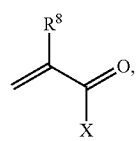

(V)

wherein

X has the meaning indicated in formula (III) and $R^8$ represents hydrogen, chlorine, bromine or optionally substituted $C_1$-$C_{10}$-alkyl, in the presence of a homogeneous, palladium-containing catalyst at a temperature ranging from about −5 to about +100° C.

2. The process according to claim 1, wherein $R^1$ represents hydrogen or chlorine, $R^2$ represents hydrogen, fluorine, chlorine or bromine, $R^3$ represents hydrogen or chlorine and $R^4$ represents fluorine or chlorine, at least one of the radicals $R^1$, $R^2$ and $R^3$ being other than hydrogen, $R^5$ represents hydrogen, methyl, ethyl, isopropyl or benzyl, $R^6$ and $R^7$ represent methyl or ethyl, $R^8$ represents hydrogen or methyl and $A^\ominus$ represents an equivalent of chloride, hydrogensulfate or acetate or ½ an equivalent of sulfate.

3. The process according to claim 1, wherein, the palladium-containing catalyst is selected from the group consisting of $PdCl_2$, $PdBr_2$, $Pd(NO_3)_2$, $H_2PdCl_4$, $Pd(CH_3COO)_2$, $Na_2PdCl_4$, $K_2PdCl_4$, Pd(II) acetylacetonate, tetra-(trisphenylphosphine)Pd, and tris-(dibenzylidene-acetone)$Pd_2$ and the palladium-containing catalyst is used in an amount ranging from about 0.001 to about 10 mol %, based on the diazonium salt of the formula (IV).

4. The process according to claim 1, wherein the diazonium salt of the formula (IV) is prepared from a corresponding aniline by reaction with sodium nitrite in acidic, aqueous solution or by reaction with an alkyl nitrite in acidic methanol and the salt is employed in the form of a reaction mixture obtained during its preparation.

5. The process according to claim 1, wherein from about 0.5 to about 2 moles of the compound of the formula (V) are employed, per mole of diazonium salt of the formula (IV).

6. The process according to claim 1, wherein the process is carried out without a base.

7. A process for preparing a compound of formula (III)

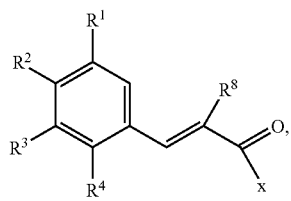
(III)

wherein $R^1$, $R^2$, $R^3$ and $R^4$ are identical or different and in each case represent hydrogen, fluorine, chlorine or bromine, at least two of these radicals being other than hydrogen and X represents $OR^5$ where $R^5$ hydrogen; and $R^8$ represents hydrogen, chlorine, bromine or optionally substituted $C_1$-$C_{10}$-alkyl, the process comprising: reacting (1) a diazonium salt of the formula (IV)

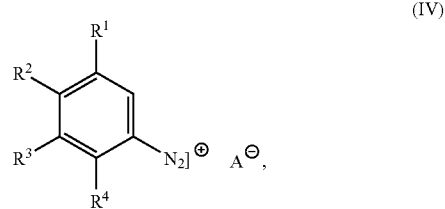
(IV)

wherein $R^1$, $R^2$, $R^3$ and $R^4$ have the meaning indicated in formula (III) and $A^\ominus$ represents an equivalent of halide, hydrogensulfate, nitrate, acetate or tetrafluoroborate ions or ½ an equivalent of sulfate ions or ⅓ an equivalent of phosphate ions, with (2) a compound of the formula (V)

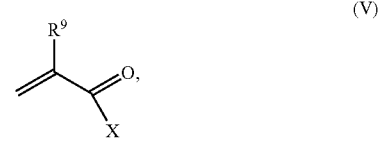
(V)

wherein

X has the meaning indicated in formula (III) and $R^8$ represents hydrogen, chlorine, bromine or optionally substituted $C_1$-$C_{10}$-alkyl, in the presence of a homogeneous, palladium-containing catalyst at a temperature ranging from about −5 to about +100° C.

* * * * *